(12) United States Patent
Yuval (10) Patent No.: US 10,688,290 B1
(45) Date of Patent: Jun. 23, 2020

(54) PERSONAL ANTI-WRINKLE DEVICE (71) Applicant: DEAD SEA PREMIER COSMETICS LABORATORIES LTD., Shoham (IL)

(72) Inventor: Yaneev Yuval, Shoham (IL)

(73) Assignee: DEAD SEA PREMIER COSMETICS LABORATORIES LTD., Shoham (IL)

( * ) Notice: Subject to any disclaimer, the term of this patent is extended or adjusted under 35 U.S.C. 154(b) by 0 days.

(21) Appl. No.: 16/426,000

(22) Filed: May 30, 2019

(51) Int. Cl.
| A61M 35/00 | (2006.01) |
| A61N 1/40 | (2006.01) |
| A61N 5/06 | (2006.01) |
| A45D 44/22 | (2006.01) |

(52) U.S. Cl.
CPC ........... *A61M 35/003* (2013.01); *A45D 44/22* (2013.01); *A61N 1/40* (2013.01); *A61N 5/0616* (2013.01); *A45D 2200/205* (2013.01); *A61M 2205/051* (2013.01); *A61M 2205/368* (2013.01); *A61M 2210/04* (2013.01); *A61N 2005/0644* (2013.01); *A61N 2005/0651* (2013.01); *A61N 2005/0663* (2013.01)

(58) Field of Classification Search
CPC .. A61M 35/003; A61M 35/006; A61M 35/00; A61M 2205/051; A61M 2205/368; A61M 2205/36; A61M 2210/04; A61H 7/003; A61H 7/004; A45D 44/22; A45D 2200/10; A45D 2200/1036; A45D 2200/1045; A45D 2200/155; A45D 2200/20; A45D 2200/205; A61N 1/40; A61N 1/403; A61N 5/00; A61N 5/025; A61N 5/06; A61N 5/0616; A61N 5/062; A61N 2005/063; A61N 2005/0635; A61N 2005/0644; A61N 2005/0651; A61N 2005/0663
USPC ......................................................... 604/20
See application file for complete search history.

(56) References Cited

U.S. PATENT DOCUMENTS

| 2004/0133251 | A1* | 7/2004 | Altshuler | ............. | A61B 18/203 607/88 |
| 2008/0183167 | A1* | 7/2008 | Britva | .................. | A61B 18/042 606/41 |
| 2014/0343574 | A1* | 11/2014 | Ignon | ................... | A61B 17/545 606/131 |
| 2015/0360014 | A1* | 12/2015 | Decaux | ............... | A61M 35/003 604/20 |
| 2019/0000539 | A1* | 1/2019 | Messerly | ......... | A61B 17/07207 |
| 2019/0133673 | A1* | 5/2019 | Boll | ....................... | A61B 5/015 |

* cited by examiner

Primary Examiner — Jason E Flick
(74) Attorney, Agent, or Firm — Mark M. Friedman

(57) ABSTRACT

A handheld device, including: (a) a housing including a grip portion and a head portion; (b) at least one radiofrequency (RF) contact disposed on the head portion; and (c) a capsule holder adapted to hold a capsule in a coupling arrangement.

17 Claims, 6 Drawing Sheets

PERSONAL ANTI-WRINKLE DEVICE

FIELD OF THE INVENTION

The present invention relates to a cosmetic skin device and, more particularly, to a handheld, dual function, electrochemical skin therapy device.

BACKGROUND OF THE INVENTION

Many skin therapy devices are known in the art. Furthermore, cosmetic, therapeutic, medicinal, etc. skin applications are known in the art.

Glossary

Therapy—treatment to help a person get better from the effects of a disease or injury:

Therapeutic—having a healing effect; tending to make a person healthier

Cosmetics—substances that you put on your face or body that are intended to improve your appearance.

Cosmetic—used to refer to substances or treatments that are intended to improve your appearance.

Medicinal—Medicinal substances are used to cure illnesses.

SUMMARY OF THE INVENTION

There is a much sought after need to slow the aging process of the skin and body and/or to make the skin and body look younger and feel more youthful. The purpose of the instantly described product is to provide an answer to this need through an integrated electronic-cosmetic, home-use anti-aging device that provides firming and tightening of facial skin and other areas of the body, as well as correcting other signs of age.

According to the present invention there is provided a handheld device, including: (a) a housing including a grip portion and a head portion; (b) at least one radiofrequency (RF) contact disposed on the head portion; and (c) a capsule holder adapted to hold a capsule in a coupling arrangement.

According to further features in preferred embodiments of the invention described below the device is configured for, at least, effecting a dual functionality of concurrently applying the capsule to skin of a user and radiating radiofrequency waves to a same area of the skin of the user.

According to still further features in the described preferred embodiments the at least one RF contact is configured to radiate radiofrequency waves when the device is activated.

According to still further features the capsule is comprised of a capsule material that can be applied to skin of a user. According to still further features the capsule material includes one of: a cosmetic material, a therapeutic material and a combination of cosmetic and therapeutic material.

According to still further features the capsule material is in a semi-solid state that rubs off onto the skin when applied. According to still further features the capsule material is adapted to melt as a result of heat emitted from the at least one RF contact when activated.

According to still further features the at least one RF contact includes two RF contacts spaced apart on the head portion, and the capsule holder disposed there-between.

According to still further features the capsule is further comprised of a clip adapted to lock onto the capsule holder, wherein the capsule material is attached to the clip. According to still further features the clip includes a planar member having a first surface and a second surface, the second surface being an opposing surface to the first surface and wherein the capsule material is mounted on the first surface.

According to still further features the second surface includes connector pieces adapted to couple the clip to the capsule holder. According to another embodiment the planar member includes a lip running along the edge of the planar member, the lip adapted to slide into a corresponding groove of the capsule holder.

According to still further features the capsule is a single-use capsule.

According to still further features the device further includes: (d) at least one light emitting diode (LED) disposed on the head portion. According to still further features the at least one LED includes a red LED. According to still further features the red LED is adapted to convey red light therapy (RLT) concurrently to the same area of the skin.

According to still further features the grip portion further includes a power button with a selectable power setting. According to still further features the device is wireless and rechargeable.

BRIEF DESCRIPTION OF THE DRAWINGS

Various embodiments are herein described, by way of example only, with reference to the accompanying drawings, wherein.

DESCRIPTION OF THE PREFERRED EMBODIMENTS

The principles and operation of a handheld, skin therapy device according to the present invention may be better understood with reference to the drawings and the accompanying description.

Figure 1:
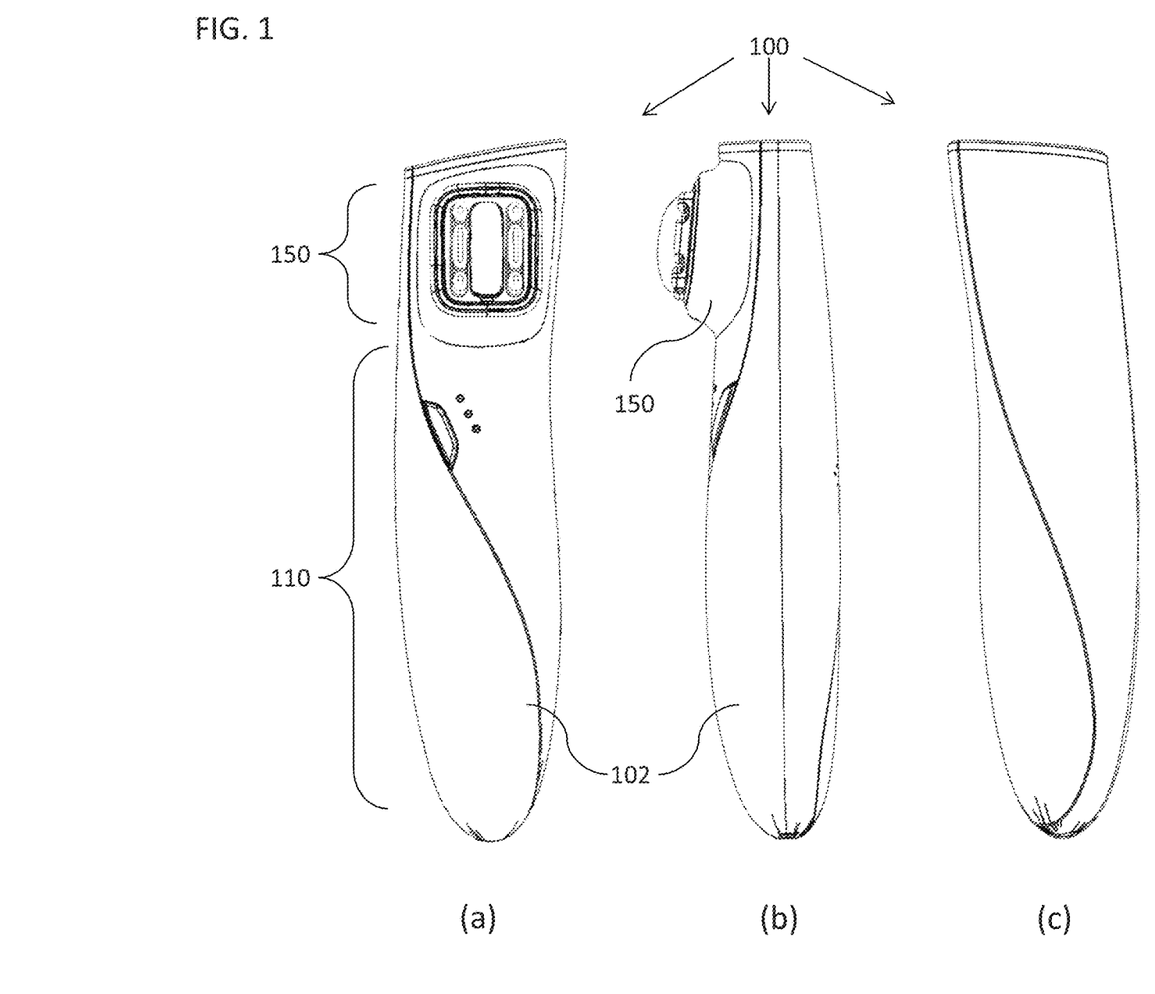
FIG. 1 is a handheld, wireless skin therapy device 100, from three views.

Referring now to the drawings, FIG. 1 shows a handheld, wireless skin therapy device 100, from three views. FIG. 1 (a) is a front view, FIG. 1 (b) is a side view and FIG. 1 (c) is a back view. Device 100 has a housing 102 which encompasses a grip portion 110 and head portion, also referred to herein as a device head 150.

Figure 2:
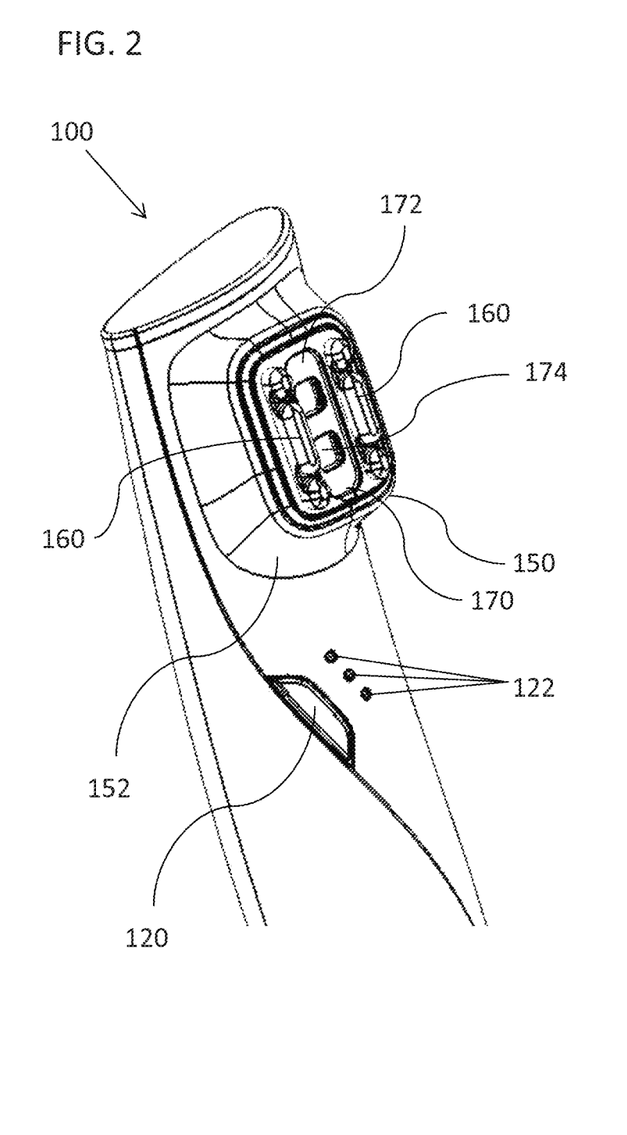
FIG. 2 is a close-up view of the upper portion of device 100 (without a capsule)

FIG. 2 illustrates a close-up view of the upper portion of device 100 (without a capsule). The device head 150 includes the primary components of the device. Namely, at least one radio frequency (RF) contact 160 and a capsule holder 170. In the depicted embodiment, two RF contacts 160 are disposed on the device head with the capsule holder 170 disposed there-between. The capsule holder is adapted to hold a capsule 200 in a coupling arrangement.

The capsule 200 is comprised of a material that can be applied to the skin. The material may be a cosmetic material, a therapeutic material or a combination of cosmetic and therapeutic material. The applicator device 100 is configured for, at least, effecting a dual functionality of concurrently applying the material of capsule 200 to skin of a user and radiating radiofrequency waves to the same area of skin of the user.

In preferred embodiments, device 100 is an over the counter (OTC) device that emits RF energy, together with an anti-aging capsule for use in the field of dermatology for the treatment of wrinkles. The device combines the two technologies of RF conductive power and disposable, single-use, anti-aging capsule. Both technologies (RF and capsule) work in synergy with each other to provide maximum results. Capsules enable personalizing the treatment with capsules being used for different skin concerns.

Although the term "anti-aging" is used to characterize the therapeutic properties of the capsules 200, it is made clear that the capsules may contain any type of cosmetic, medicinal or therapeutic compound or a combination thereof. The material of the capsule is preferably provided in a semi-solid state that rubs off onto the skin when applied with the applicator device (e.g. with gentle, circular movements of the device head coupled with a capsule over target areas on the face, neck and/or forehead). In preferred embodiments, heat from the RF contacts melts the capsule material so that it is easier to apply and absorbed more easily.

RF contacts 160 emit radio frequency waves. One exemplary RF device is the radiofrequency-emitting Thermafine-Lift device (GrupoSolila'ser, S.L.) which emits interwoven bipolar radiofrequency waves from 4 to 8 MHz. It is made clear that any relevant RF emitting components can be used. The RF contacts 160, when activated, radiate RF waves that penetrates beneath the skin surface. Preferably, the RF components of the instant embodiment emit radiofrequency waves from 0.5 to 1.5 MHz.

Currently there are numerous techniques available for rejuvenating the skin: chemical peels, dermoabrasion, different types of laser, etc; and recently, radiofrequency. The RF technique produces an electrical current which generates heat due to the resistance by the components of the dermis and subcutaneous tissues, with it being possible for said heat to be originated selectively from the papillary dermis to the subcutaneous adipose tissue. The depth of its reach and the effects depend on the geometry and size of the electrode and the conductive properties of the tissue treated, respectively. High frequency radiofrequency has been used in cosmetic medicine for the treatment of facial wrinkles, and naso-labial creases, in order to improve the laxity of the neck and to raise eyelids.

Capsule holder 170 is located between the two RF contacts 160. The holder is formed from a flat plate of sturdy material (such as PVC or metal) 172 with two apertures 174 formed therein.

Figure 3:
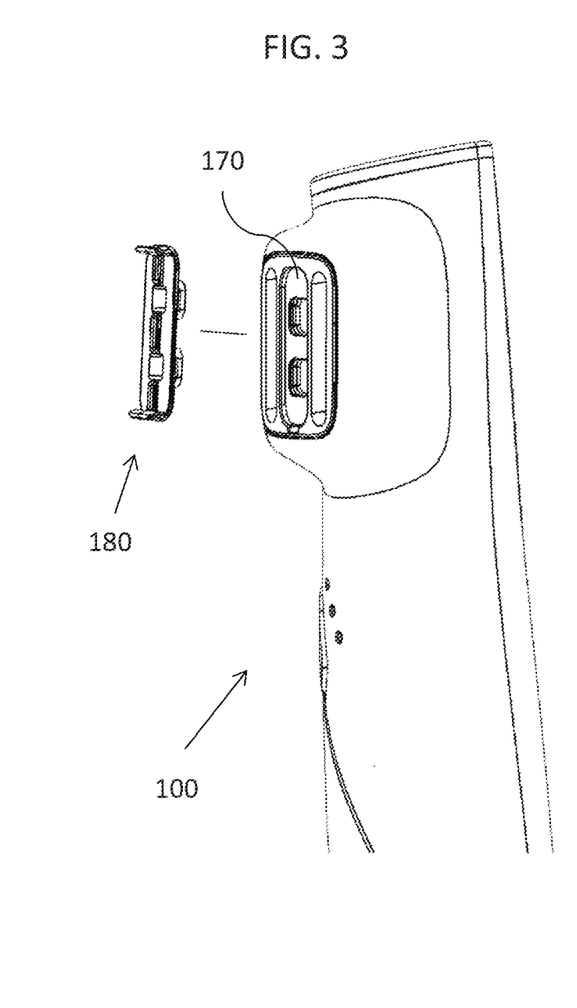
FIG. 3 is a view of the device with a corresponding clip.
Figure 3A:
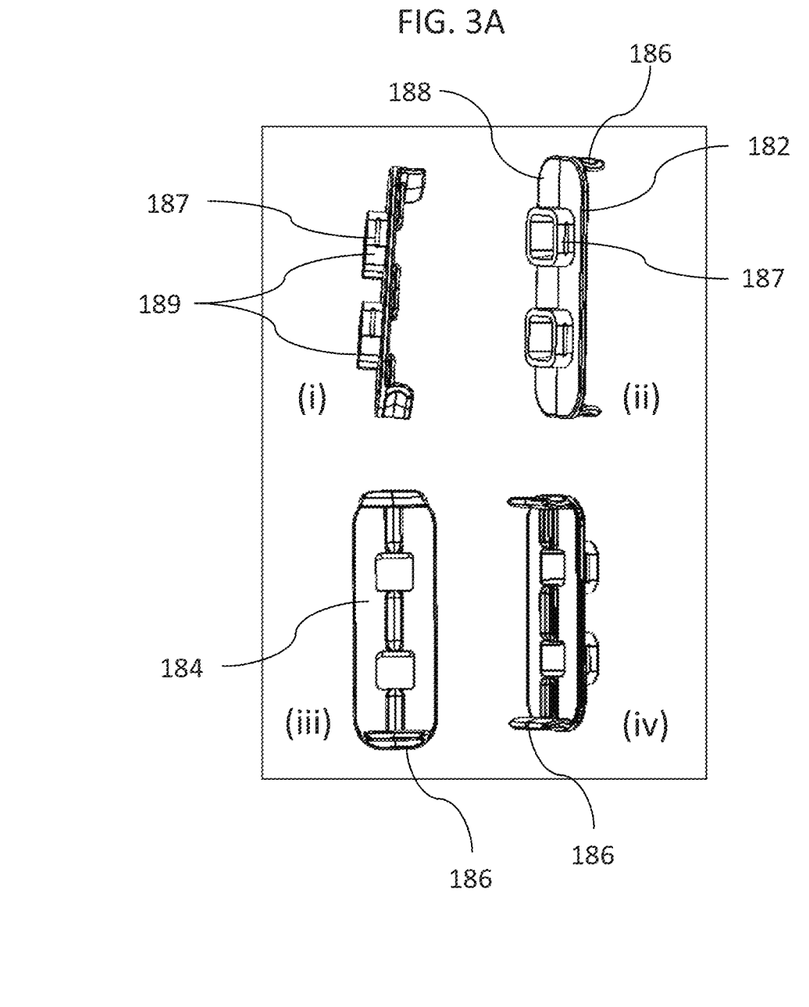
FIG. 3A show 4 magnified views of the clip.

FIG. 3 shows the device with a corresponding clip. A corresponding clip 180 is adapted to lock into capsule holder 170. Capsule material is mounted on (attached, adhered or otherwise coupled to) one side of the clip 180. FIG. 3A illustrates 4 magnified views of the clip 180. View 3A(i) is a side or profile view. View 3A(ii) is an isometric back view of the clip, of the attachment side. View 3A(iii) is a front view of the capsule side. View 3A(iv) is an isometric front/capsule side view.

Clip 180 includes a thin, flat, planar member 182. A first surface 184 of the planar member 182, referred to hereafter as the front or capsule surface 184. The front/capsule surface is best seen in FIG. 3A(iii). The capsule surface 184 is book-ended with extension pieces 186 which extending perpendicular to the planar member 182. The capsule material (chemical compound, medicament, etc.) is disposed on the capsule surface 184 of the planar member.

A second surface 188 of the planar member 182, is the opposing surface to the capsule surface 184. The second surface is referred to hereafter as the back or connecting surface 188. Two, raised, connector pieces 189 protrude from the connecting surface 188. The connector pieces have a corresponding shape and size to the apertures 174. Each connector piece further includes a slight lip 187 which secures the connector pieces inside the apertures, as is well known in the art.

In an alternative embodiment, the connector pieces are magnetized, such that the coupling arrangement is a magnetic coupling arrangement. In such embodiments, there is no lip 187. In embodiments, a flat covering piece, not shown, fits fixedly over the capsule holder to protect the holder from dirt and other contaminants.

In another alternative embodiment, the connector pieces are spring-loaded, such that when the capsule is uncoupled from the device head, the spring biases the capsule away from the device head.

Figure 4:
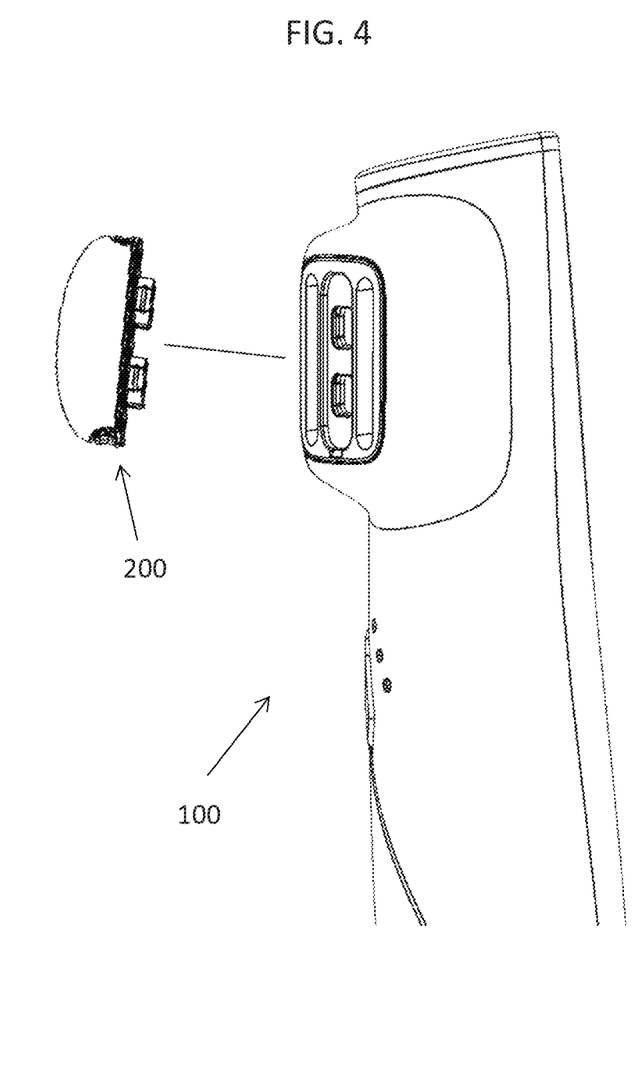
FIG. 4 is an exploded view of device 100 and a capsule 200.
Figure 4A:
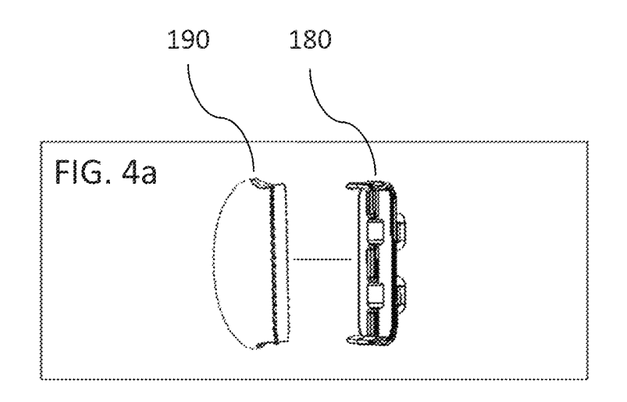
FIG. 4(a)-(e) are various views of capsule 200.
Figure 4B:
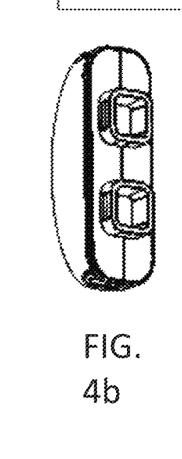
Figure 4C:
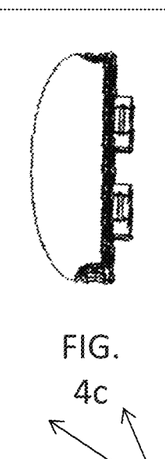
Figure 4D:
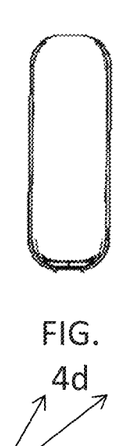
Figure 4E:
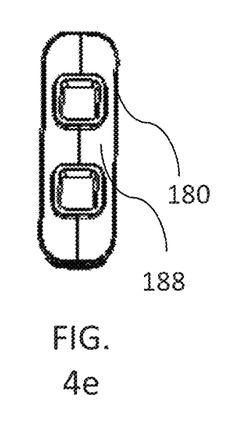

FIG. 4 illustrates an exploded view of device 100 and a capsule 200. FIG. 4(a) illustrates an exploded view of the capsule 200 with the clip 180 and capsule material 190 shown separately. FIG. 4(b) is a back isometric view of capsule 200. FIG. 4(c) is a side view of the capsule 200. FIG. 4(d) is a front view of the capsule 200 and FIG. 4(e) is a back view of the capsule. In some embodiments, such as described in FIG. 4, the capsule material 190 is flat on the back, connecting side and convex on the front, application side.

In general, clip 180 and capsule material 190 are intended to be provided as a single unit for a single use. Once the capsule material is expended by application to the skin, the clip is to be disconnected from the holder and disposed of. Clip 180 and capsule material 190 are also referred to collectively as capsule 200. Dual function, handheld therapy device 100 is used in conjunction with single-use capsules 200.

The head portion or device head 150 includes at least one light emitting diode (LED). In embodiments, an LED indicator 152 (see FIG. 2) that is located below the treatment platform of the device head, on the slope between the treatment area and the rest of the housing. Preferably the LED is a red LED. Red LED light is known to have a therapeutic effect on skin. Red light therapy (RLT) is a controversial therapeutic technique that uses red, low-level wavelengths of light to treat skin issues, such as wrinkles, scars, and persistent wounds, among other conditions.

In embodiments, the LED 152 simply acts as an indicator that the device in active. Additionally or alternatively, LED 152 provides a therapeutic effect in addition to the therapeutic effect of the medicinal/cosmetic capsule and the RF waves. In embodiments, more than one LED is located on the device head. In embodiments, the LED or LEDs include colors other than red. In embodiments, the LEDs include red lights as well as one or more LEDs of colors other than red. Some additional exemplary colors include, but are not limited to: blue, purple, white, green blue, green and yellow.

Method of Use

The treatment (with or without the LED light therapy) is effected by a combination of a chemical reaction between the gel and capsule together with the radio waves (an in some cases, light) and the electrically conductive properties of the gel. Together, these components work in a synergetic manner to enhance penetration of the active elements to the treatment area. In some instances, the RF contacts heat up, and positively affect the chemical material of the capsule 200, whereby the capsule material softens (melts), and can be applied to the skin surface more easily and be absorbed more readily.

The device and capsule are intended to be used on the home for a personal treatment of the skin. Usually the skin of the face and neck are targeted for application of the capsule treatment simultaneously with the RF treatment. The steps for treatment, according to an exemplary embodiment, are as follows:

Step 1: Clean and dry the face;
Step 2: Connect a new disposable capsule to the device head;
Step 3: Apply conductive gel on the treatment area;
Step 4: Press the activation button and set the treatment level;
Step 5: Treat skin zone: place the device tip on the treatment area (the device head will illuminate in red, indicating that energy is being delivered). Move the device in constant, circular movements. The device will vibrate after 4 minutes to indicate that the user can move to the next treatment zone.
Step 6: After use: dispose of the capsule and clean the device tip from any remaining gel.

The instantly described device is intended for use in dermatology for the treatment of various issues including wrinkles, pigmentations, pore reduction, inflammation as well as skin lifting and firming and other signs of aging of the skin or damage to the skin.

One example of the composition of the capsule is DEIONIZED WATER, PROPYLENE GLYCOL, GLYCERINE, SODIUM STEARATE, UREA, PEG-12 DIMETHICONE, ETHANOLAMINE, SODIUM GLYCEROPHOSPHATE, ALOE BARBADENSIS. It is clear that there aforementioned composition is merely exemplary and any applicable composition can be used instead.

Housing

The grip portion 110 of the device houses various structural and functional components. The grip portion is where the user holds the device. The housing 102 further encompasses a power button 120, which has three power ON settings (low, medium, high) and an OFF setting. Next to the power button are three LED indicator lights 122 which reflect the current power state.

In the exemplary embodiment, the power button is a push button actuator. Pushing the power button 120 one time turns the device onto the low setting. One of indicator lights 122 turns on, indicating the low power setting. Pushing the button a second time changes the setting to the medium power setting and a second light of the indicator lights 122 turns on. Pushing the power button a third time results in the device being moved into the high power setting and the third indicator light turns on. Of course, other actuator configurations are considered to be within the scope of the invention. For example, a movable selector with four distinct positions (off, $1^{st}$, $2^{nd}$ and third power levels) is another potential power actuator mechanism.

Once the power setting has been chosen, the device remains active at the desired setting for a predetermined amount of time. Thereafter, the device automatically switches off and the indicator lights 122 turn off. The user can manually switch off the device by pressing the power button 120 a fourth time.

The duration of activity for the device may be pre-configured by the manufacturer. Alternatively or additionally, the duration of activity may be programmable post manufacture. Further alternatively or additionally, the duration of activity may be user programmable. Additionally or alternatively, the duration of activity may be configured relative to the power setting.

Additionally or alternatively, the duration of activity may be controlled or configured according to the type of capsule/medicament attached to the device head. In embodiments, the applicator device 100 has one of a plurality of means for recognizing what type of capsule is attached to the device and, once recognized, operates according to predefined parameters.

The plurality of means for recognizing capsule type can include mechanical means, electrical means, electromechanical means, optical means, radio signals and any combination thereof. Cessation of activity may alternatively or additionally (e.g. as a backup means or failsafe mechanism) be controlled based on the device sensing that the capsule has been used up/dissolved/fully applied, at which point the device switches off.

Figure 5:
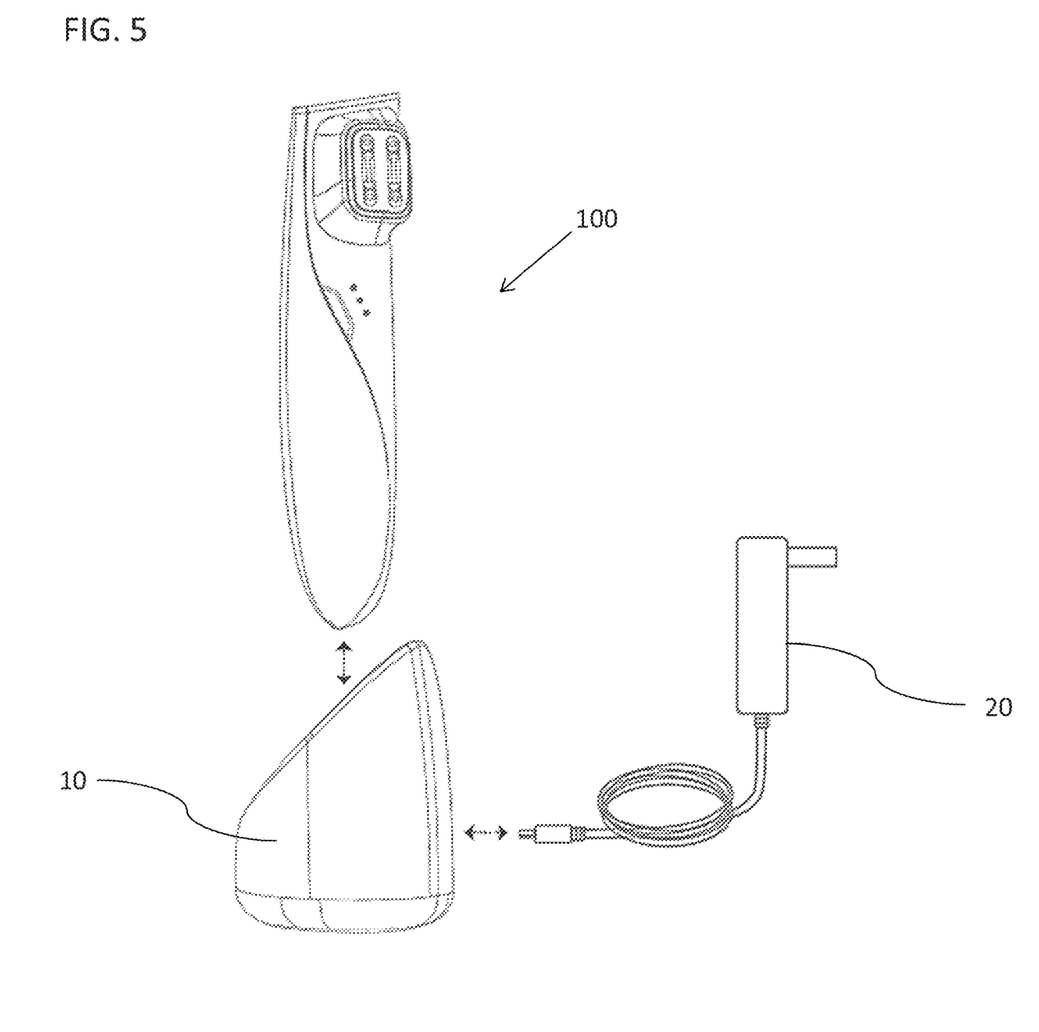
FIG. 5 is an illustration of device 100 and essential accessories according to one exemplary embodiment.

FIG. 5 illustrates device 100 and essential accessories according to one exemplary embodiment. FIG. 5 shows a handheld, wireless skin therapy device 100, a charging cradle 10 and a power adapter 20. In the depicted embodiment, the skin device is wireless with a rechargeable battery. For charging, the device 100 is docked in the cradle 10 which draws power from the power grid by means of the power adapter 20, which is plugged into a wall socket power outlet.

In an alternative embodiment, there is disclosed a wired device which is connected directly to a power outlet via an adapter similar to adapter 20. Aside for the power arrangement, the functional features and structure of the wired device is the same mutatis mutandis to the wireless device. Both wireless and wired devices are within the scope of the invention, and any description set forth herein with regards to wireless devices is incorporated via reference as if set forth fully with regards, mutatis mutandis, to wired devices.

Figure 6A:
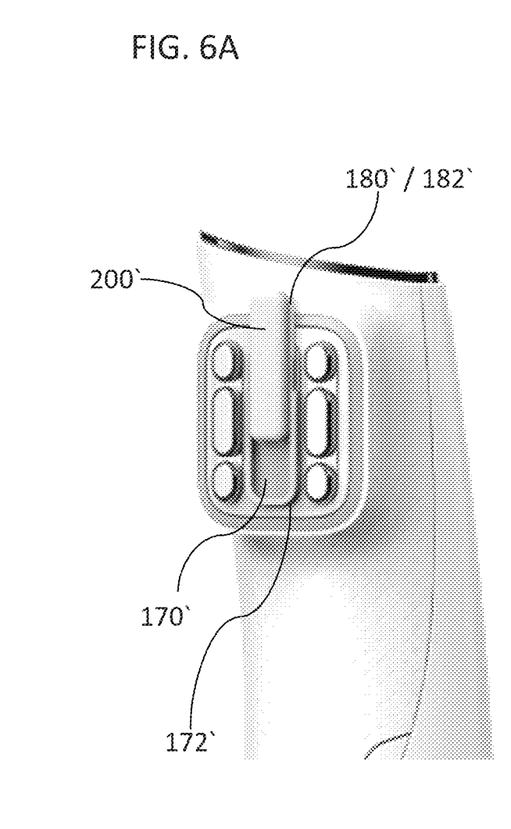
FIG. 6A-B are views of a second embodiment of the invention embodied in applicator device 100' and capsule 200'.
Figure 6B:
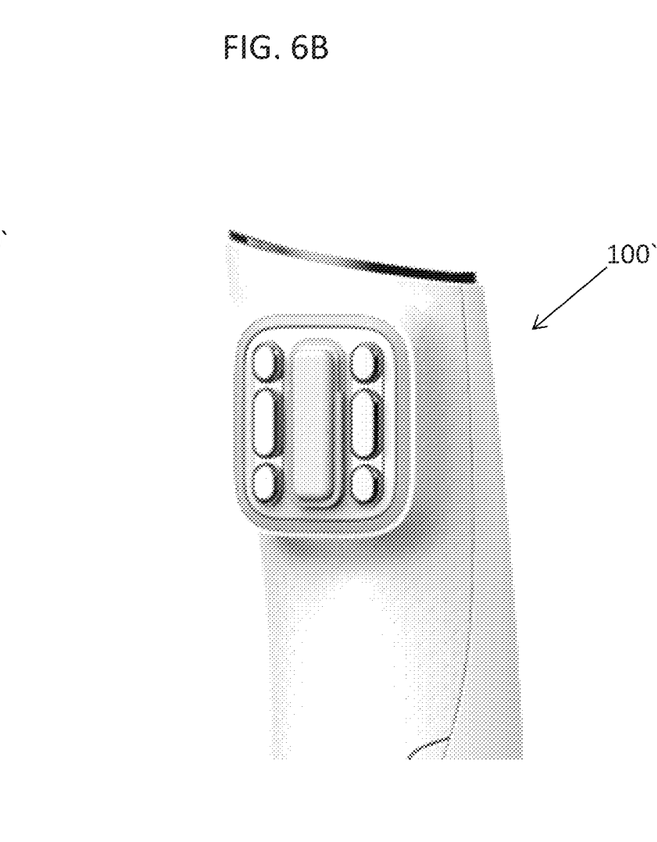

Another configuration is shown in FIG. 6A-B, including a second embodiment of the invention embodied in an applicator device 100' and a capsule 200'. FIG. 6A illustrates capsule 200' partially inserted into a capsule holder 170' of the device 100'. FIG. 6B depicts the capsule fully inserted into the capsule holder of the device. The applicator 100' is almost identical to applicator device 100, with the only difference being the manner in which the capsule couples with the applicator head. The coupling arrangement depicted in FIGS. 6A-B is a sliding arrangement. The capsule holder 170' includes a U-shaped protuberance 172' which defines a groove between the flat body of the capsule holder and the protuberance. A clip 180' of capsule 200' includes a planar member 182' with a lip running along the edge of the planar member. The capsule 200' is coupled to the device 100' by sliding the capsule into the holder such that the lip of the capsule engages with the groove of the holder. The lip may be defined as an edge of the planar member that is not covered by capsule material on the capsule side.

The following are exemplary components making up the power system of the rechargeable/wireless embodiments of the device. The housing holds a battery (not shown), e.g. a 14500 AA size rechargeable Li-ion cylindrical battery. The battery is an 800 mAh, 3.6V DC, type 14500 cylindrical Lithium-ion rechargeable cell, having external dimensions match that of a AA lead acid battery and is available from Tenergy of Fremont Calif. under model designation 30001-0. The estimated number of charge-discharge cycles is 500 cycles. Preferably the device includes a charger circuit such as an in-circuit Li-ion charger, model MCP7387T-FCI/MF available from Microchip. The LED indicator light are green clear 0603 surface mount LEDs available from LITE-ON, PN LTST-C190KGKT. The PWMs are MOSFET N-CH 28V 1.6A SC70-3-filtered with inductor power 68UH 0.62A SMD available from Bournes, PN SRR5028-680Y.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A skin care system, the system comprising:
    (a) a handheld device, comprising: a housing including a grip portion and a head portion, said head portion including a treatment platform with at least one radiofrequency (RF) contact and a capsule holder side-by-side thereon; and
    (b) a consumable, skin application capsule, said capsule comprised of capsule material that is adapted to rub off onto skin of a user and said capsule holder adapted to releasably hold said capsule in a coupling arrangement;
    wherein the system is configured to output RF radiation at the same time that said capsule material is being applied to said skin of said user.

2. The system of claim 1, wherein the device is configured for, at least, effecting a dual functionality of concurrently applying said capsule to skin of a user and radiating radiofrequency waves to a same area of said skin of said user.

3. The system of claim 2, further comprising:
    (d) at least one light emitting diode (LED) disposed on said head portion.

4. The system of claim 3, wherein said at least one LED includes a red LED.

5. The system of claim 4, wherein said red LED is adapted to convey red light therapy (RLT) concurrently to said same area of said skin.

6. The system of claim 1, wherein said at least one RF contact is configured to radiate radiofrequency waves when the device is activated.

7. The system of claim 1, wherein said capsule material includes one of: a cosmetic material, a therapeutic material and a combination of cosmetic and therapeutic material.

8. The system of claim 1, wherein said capsule material is in a semi-solid state that rubs off onto said skin when applied.

9. The system of claim 1, wherein said capsule material is adapted to melt as a result of heat emitted from said at least one RF contact when activated.

10. The system of claim 1, wherein said at least one RF contact includes two RF contacts spaced apart on said head portion, and said capsule holder disposed there-between.

11. The system of claim 1, wherein said capsule is further comprised of a clip adapted to lock onto said capsule holder, wherein said capsule material is attached to said clip.

12. The system of claim 11, wherein said clip includes a planar member having a first surface and a second surface, said second surface being an opposing surface to said first surface and wherein said capsule material is mounted on said first surface.

13. The system of claim 12, wherein said second surface includes connector pieces adapted to couple said clip to said capsule holder.

14. The system of claim 12, wherein said planar member includes a lip running along the edge of said planar member, said lip adapted to slide into a corresponding groove of said capsule holder.

15. The system of claim 1, wherein said grip portion further includes a power button with a selectable power setting.

16. The system of claim 1, wherein the device is wireless and rechargeable.

17. The skin care system of claim 1, wherein said at least one RF contact is adapted to generate heat in use and transform said capsule material from a solid state to a non-solid state.

* * * * *